United States Patent
Fukui et al.

(10) Patent No.: US 9,180,074 B2
(45) Date of Patent: Nov. 10, 2015

(54) O/W EMULSION COSMETIC

(75) Inventors: Takashi Fukui, Tokyo (JP); Takashi Kawata, Tokyo (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 13/480,581

(22) Filed: May 25, 2012

(65) Prior Publication Data

US 2012/0294912 A1    Nov. 22, 2012

Related U.S. Application Data

(63) Continuation of application No. PCT/JP2010/071047, filed on Nov. 25, 2010.

(30) Foreign Application Priority Data

Nov. 25, 2009   (JP) .................................. 2009-267497

(51) Int. Cl.

| | | |
|---|---|---|
| A61K 8/06 | (2006.01) |
| A61Q 17/04 | (2006.01) |
| A61K 8/29 | (2006.01) |
| A61K 8/27 | (2006.01) |
| A61K 8/92 | (2006.01) |
| A61K 8/19 | (2006.01) |
| A61K 8/02 | (2006.01) |
| A61K 8/31 | (2006.01) |
| A61K 8/37 | (2006.01) |
| A61K 8/58 | (2006.01) |
| A61K 8/68 | (2006.01) |
| A61K 8/81 | (2006.01) |
| A61Q 19/00 | (2006.01) |

(52) U.S. Cl.
CPC ............... *A61K 8/062* (2013.01); *A61K 8/0254* (2013.01); *A61K 8/06* (2013.01); *A61K 8/19* (2013.01); *A61K 8/31* (2013.01); *A61K 8/37* (2013.01); *A61K 8/585* (2013.01); *A61K 8/68* (2013.01); *A61K 8/8152* (2013.01); *A61Q 17/04* (2013.01); *A61Q 19/007* (2013.01); *A61K 2800/612* (2013.01)

(58) Field of Classification Search
None
See application file for complete search history.

(56) References Cited

U.S. PATENT DOCUMENTS 5,670,139 A * 9/1997 Allard et al. ..................... 424/59
5,830,481 A * 11/1998 Cauwet-Martin et al. .... 424/401
7,550,135 B2 * 6/2009 Hoshino et al. ............ 424/70.17
2003/0202948 A1 * 10/2003 Koini et al. ..................... 424/59
2005/0207999 A1    9/2005 Vernaire et al.
2006/0084586 A1 * 4/2006 Drzewinski et al. .......... 510/119
2007/0128146 A1 * 6/2007 Fujino et al. ............... 424/70.31

FOREIGN PATENT DOCUMENTS

| EP | 2 027 847 | 2/2009 |
|---|---|---|
| JP | 64-90111 | 4/1989 |
| JP | 11-012119 | 1/1999 |
| JP | 11-12131 A | 1/1999 |
| JP | 11-322564 | 11/1999 |
| JP | 2001-181136 | 7/2001 |
| JP | 2005-002076 | 1/2005 |
| JP | 2005-002077 | 1/2005 |
| JP | 2005-002078 | 1/2005 |
| JP | 2005-2078 A * | 6/2005 |
| JP | 2005-145972 | 6/2005 |
| JP | 2007-320917 | 12/2007 |
| JP | 2011-111401 | 6/2011 |

OTHER PUBLICATIONS

English Language Translation of JP 2005-002078.*
U.S. Appl. No. 13/480,570, filed May 25, 2012, Fukui, et al.
U.S. Appl. No. 13/508,392, filed May 7, 2012, Yamada, et al.
U.S. Appl. No. 13/505,558, filed May 2, 2012, Yamada, et al.
Office Action issued Aug. 14, 2012 in Japanese Patent Application No. 2009-267497 (with English-language translation).
International Preliminary Report on Patentability with Written Opinion issued on Jun. 14, 2012 in the corresponding European Application No. PCT/JP2010/071047 filed on Nov. 25, 2010.
International Search Report issued Feb. 22, 2011, in PCT/JP2010/071047.

* cited by examiner

*Primary Examiner* — Rachael E Bredefeld
*Assistant Examiner* — Dominic Lazaro
(74) *Attorney, Agent, or Firm* — Oblon, McClelland, Maier & Neustadt, L.L.P.

(57) ABSTRACT

A cosmetic composition in the form of an O/W emulsion includes: (A) 1 to 20% by weight of a plate-like powder that has been surface-treated with an alkylalkoxysilane, (B) 0.1 to 10% by weight of an oil that is solid at a temperature of 25° C., (C) 0.3 to 50% by weight of an oil selected from the group consisting of a hydrocarbon oil, an ester oil, and an ether oil, each having a viscosity of 500,000 mPa·s or less at a temperature of 25° C., (D) 0.1 to 20% by weight of a nonionic surfactant having an HLB value of 8 or less, (E) 0.05 to 10% by weight of a water-soluble polymer having a hydrocarbon group with a carbon number of 8 to 30 and an anionic group in a molecule thereof, and (F) water.

17 Claims, No Drawings

O/W EMULSION COSMETIC

CROSS REFERENCES TO RELATED APPLICATIONS

This application is a continuation of International Patent Application No. PCT/JP2010/071407, filed on Nov. 25, 2010, and claims priority to Japanese Patent Application No. 2009-267497, filed on Nov. 25, 2009, all of which are incorporated herein by reference in their entireties.

BACKGROUND OF THE INVENTION

1. Field of the Invention

The present invention relates to O/W emulsified cosmetic compositions.

2. Discussion of the Background

An organic ultraviolet absorber for efficiently absorbing ultraviolet rays and an ultraviolet protective powder for scattering ultraviolet rays have been conventionally used for protecting from ultraviolet rays. Titanium dioxide and zinc oxide have been frequently used as the ultraviolet protective powder, and need to be blended into a cosmetic composition in large quantities for protecting from ultraviolet rays. Thus, the problem is that when the cosmetic composition is applied to skin, the skin is whitened, and a dry feeling specific to powders occurs to deteriorate the texture.

In order to suppress such a dry feeling when the cosmetic composition is applied to skin, cosmetic compositions have been proposed employing a pigment that is surface-treated to reduce oil absorption, thus minimizing degreasing of sebum from skin and improving durability of the makeup, water resistance, sebum resistance, texture, ability to avoid transfer of makeup after application, and coloring, while decreasing the burden on the skin. Such compositions are proposed, for example, in Japanese Patent Application Laid-Open (JP-A) 2005-2076, JP-A 2005-2077, and JP-A 2005-2078.

However, even though such a surface-treated pigment is used, a dry feeling may not be sufficiently suppressed and a high moisture retaining property is not obtained.

SUMMARY OF THE INVENTION

In embodiments of the present invention, cosmetic compositions may include the following components (A), (B), (C), (D), (E) and (F):

(A) 1 to 20% by weight of a plate-like powder that has been surface-treated with an alkylalkoxysilane, (B) 0.1 to 10% by weight of an oil that is solid at a temperature of 25° C., (C) 0.3 to 50% by weight of an oil selected from the group consisting of a hydrocarbon oil, an ester oil, and an ether oil, each having a viscosity of 500,000 mPa·s or less at a temperature of 25° C., (D) 0.1 to 20% by weight of a nonionic surfactant having an HLB value of 8 or less, (E) 0.05 to 10% by weight of a water-soluble polymer having a hydrocarbon group with a carbon number of 8 to 30 and an anionic group in a molecule thereof, and (F) water, in which a weight ratio of component (B) to component (A), (B)/(A), is 0.01 to 5, and the composition is in the form of an O/W emulsion.

Exemplary O/W emulsified cosmetic compositions according to the present invention are uniform and smooth, allow a coating with high occlusive properties, are excellent in a moisture-retaining property, offer a favorable feeling upon use, and are high in ultraviolet protective effect.

DETAILED DESCRIPTION OF THE PREFERRED EMBODIMENTS

Other features of the invention will become apparent in the course of the following descriptions of exemplary embodiments which are given for illustration of the invention and are not intended to be limiting thereof.

In embodiments, the present invention is directed to cosmetic compositions that do not result in a dry feeling when applied to the skin, have an excellent moisture-retaining property, and have a high ultraviolet protective effect.

The present inventors developed O/W emulsified cosmetic compositions that form a coating with high occlusive properties on a skin surface, are excellent in a moisture-retaining property, offer a favorable feeling upon use, and are high in ultraviolet protective effect, by employing a plate-like powder that has been surface-treated with alkylalkoxysilane and an oil that is solid at a temperature of 25° C. at a specific ratio, and by further employing a specific liquid oil and an emulsifying agent, in combination.

In embodiments, component (A) in O/W emulsified cosmetic compositions according to the present invention is a plate-like powder that has been surface-treated with alkylalkoxysilane. Among these, a flaky powder having an average particle diameter of 0.1 to 10 μm, preferably 0.2 to 1 and having a plate ratio (average particle diameter/thickness) of 3 or more, preferably 5 to 45, and more preferably 10 to 45, is preferable. The average particle diameter is represented by the arithmetic mean of the major axis and the minor axis of a plate-like smooth surface, and calculated from the result measured for twenty arbitrary particles in an arbitrary field of view in a transmission electron microscope photograph. Similarly, the average particle thickness is calculated from the result measured for twenty arbitrary particles in the same field of view of a transmission electron microscope photograph.

Examples of plate-like powders of component (A) include plate-like zinc oxide, plate-like titanium dioxide, plate-like cerium oxide, plate-like barium sulfate, talc, mica, plate-like kaoline, sericite, muscovite, plate-like synthetic mica, phlogopite, lepidolite, biotite, lithia mica, plate-like silicic acid anhydride, plate-like hydroxyapatite, bentonite, montmorillonite, hectorite, plate-like ceramic powder, plate-like alumina, plate-like boron nitride, plate-like polymethyl methacrylate powder, lauroyl lysine, plate-like iron oxide, titanium dioxide-coated mica, titanium dioxide-treated mica, bismuth oxychloride, titanium dioxide-coated bismuth oxychloride, titanium dioxide-coated talc, argentine, titanium dioxide-coated colored mica, aluminum, and the like. Among these, from the viewpoint of ultraviolet protective effect, zinc oxide, titanium dioxide, and cerium oxide are preferable, and zinc oxide is more preferable. Zinc oxide containing iron as a trace element is even more preferable.

An alkylalkoxysilane used for treating such a plate-like powder is preferably one having a branched or linear alkyl group with a carbon number of 6 to 20, preferably 6 to 10, and more preferably 8, and an alkoxy group with a carbon number of 1 or 2, preferably 2. Among these, octyltriethoxysilane or octyltrimethoxysilane is preferable. These compounds can treat the powder more uniformly.

Methods for treating a plate-like powder with an alkylalkoxysilane are not limited and examples thereof include a wet method, a dry method, an evaporation method (a method for depositing a treating agent onto a pigment by using plasma), a gas phase method (a method for surface-treating in a gas such as air and nitrogen gas), and a mechanochemical method (a method for mechanochemically surface-treating by using apparatuses such as a ball mill, an angmill (manufactured by Hosokawa Micron Corp.) and a hybridizer (manufactured by Nara Machinery Co., Ltd.)), and the like.

Among these, a wet method involving mixing a plate-like powder with alkylalkoxysilane in organic solvents such as a lower alcohol, hexane, acetone, toluene, cyclohexane, xylene, dimethylformamide, N-methylpyrrolidone, carbon dioxide, and terpenes, removing the organic solvents by heating and decompression after the uniformly mixing, and preferably heat-treating at a temperature of 80 to 250° C., is preferred. By employing such a method, the treatment can be performed more uniformly.

The throughput of alkylalkoxysilane is preferably 2 to 10% by weight, and more preferably 2 to 7% by weight based on a total weight of the treated plate-like powder.

One or more of types of component (A) may be used and included in an amount of 1 to 20% by weight, preferably 5 to 15% by weight, and more preferably 9 to 12% by weight based on a total weight of the composition from the viewpoint of forming a uniform coating in combination with component (B), an oil that is solid at a temperature of 25° C., discussed below.

In embodiments, component (B) in O/W emulsified cosmetic compositions according to the present invention is an oil that is solid at a temperature of 25° C. Examples thereof include a fatty alcohol, a fatty acid, a fatty amide derivative, a fatty amine derivative, and the like.

Fatty alcohols preferably include saturated fatty alcohols with a carbon number of 12 to 24, such as lauryl alcohol, myristyl alcohol, cetanol, stearyl alcohol, and behenyl alcohol. Fatty acids preferably include saturated fatty acids with a carbon number of 12 to 24 such as lauric acid, myristic acid, palmitic acid, stearic acid, and behenic acid. Fatty amide derivatives preferably include a ceramide such as natural ceramides of type I to type VI, N-(2-hydroxy-3-hexadecyloxypropyl)-N-2-hydroxyethylhexadecanamide, N-(2-hydroxy-3-hexadecyloxypropyl)-N-2-hydroxyethyldecanamide, and analogs thereof. Fatty amine derivatives preferably include a sphingosine such as sphingosine, dihydrosphingosine, phytosphingosine, dehydrosphingosine, dehydrophytosphingosine, sphingadienine, and N-methyl compounds or N,N-dimethyl compounds thereof, 1-(2-hydroxyethylamino)-3-isostearyloxy-2-propanol, and the like. A sterol such as cholesterol, stigmasterol, and ergosterol may be also used.

Hydrocarbon-based, ester-based, natural and synthetic waxes such as silicone waxes may be used. Examples thereof include animal waxes such as beeswax and spermaceti; vegetable waxes such as carnauba wax, candelilla wax, rice wax and Japan wax; mineral waxes such as montan wax, ozokerite, ceresin, paraffin wax and microcrystalline wax; synthetic waxes such as polyethylene wax, Fischer-Tropsch wax, hydrogenated castor oil, hydrogenated jojoba oil, stearic acid amide, phthalic anhydride imide and silicone wax, and the like.

In embodiments, component (B) does not include an organic ultraviolet absorber.

One or more types of component (B) may be used and included in an amount of 0.1 to 10% by weight, preferably 0.3 to 5% by weight, and more preferably 0.5 to 1.5% by weight based on a total weight of the composition from the viewpoint of coat-forming properties.

In embodiments of O/W emulsified cosmetic compositions according to the present invention, a weight ratio between component (A) and component (B) is (B)/(A)=0.01 to 5, preferably 0.02 to 1, and more preferably 0.05 to 0.15.

While not being limited to a particular theory, when the weight ratio between the component (A) and the component (B) is in this range, it is believed that the size of oil drops in an O/W emulsified cosmetic composition decreases and the O/W emulsified cosmetic composition is applied to skin more uniformly to allow high moisture retaining property by improving occlusive properties. It is believed that a coating with such occlusive properties is not formed using a silicone-treated powder and/or a fluorine-treated powder, which are frequently used and cause problems of texture such as a dry feeling.

In embodiments, component (C) in O/W emulsified cosmetic compositions according to the present invention is an oil that is a liquid at a temperature of 25° C. Exemplary oils have a viscosity of more than 0 and 500,000 mPa·s or less, preferably 100,000 mPa·s or less, and more preferably 5 to 1,000 mPa·s at a temperature of 25° C. Exemplary oils are selected from the group consisting of a hydrocarbon oil, an ester oil and an ether oil.

Viscosity may be a value measured by a Brookfield (B type) viscometer.

Specific examples thereof include hydrocarbon oils such as liquid paraffin, liquid isoparaffin, hydrogenated polyisobutene, heavy liquid isoparaffin, Vaseline, squalane, n-octane, n-heptane, isododecane and cyclohexane; ester oils such as diisostearyl malate, octyldodecyl lactate, isotridecyl isononanoate, octyldodecyl myristate, isopropyl palmitate, isopropyl isostearate, butyl stearate, myristyl myristate, isopropyl myristate, octyldodecyl myristate, di-2-ethylhexyl adipate, diisopropyl sebacate, neopentylglycol dicaprate and tricaproin; and ether oils such as dioctyl ether, ethylene glycol monolauryl ether, ethylene glycol dioctyl ether and glycerol monooleyl ether.

In embodiments, component (C) is free of organic ultraviolet absorbers such as 2-ethylhexyl paramethoxycinnamate.

One or more types of component (C) may be used and included in an amount of 0.3 to 50% by weight, preferably 0.5 to 40% by weight, further preferably 0.3 to 10% by weight, and more preferably 5 to 10% by weight based on a total weight of the composition from the viewpoint of adaptation to skin during the application.

A weight ratio between component (B) and component (C) is preferably (B)/(C)=0.0025 to 2, and more preferably 0.01 to 1 from the viewpoint of the solubility of the component (B), moderate control of the crystallization of the component (B), improvement of adhesion to the component (A), and formation of a coating with high occlusive properties.

In embodiments, component (D) in O/W emulsified cosmetic compositions according to the present invention is a nonionic surfactant having an HLB value of 8 or less, preferably 4 to 8, and more preferably 4 to 5. Here, HLB is an index for denoting a balance between hydrophilic property and lipophilic property (Hydrophile-Lipophile Balance), and defined by the following expression from R. Oda, K. Teramura, Synthesis of Surface-Active Agents and Their Application, Makishoten, 1960, p. 501:

$$HLB = (\Sigma \text{ inorganic value}/\Sigma \text{ organic value}) \times 10$$

Examples of such a nonionic surfactant include sorbitan fatty acid esters (e.g., sorbitan monoisostearate, sorbitan monooleate, sorbitan monopalmitate, sorbitan monostearate, sorbitan sesquioleate, and sorbitan trioleate), glycerin fatty acid esters (e.g., glyceryl monostearate, glyceryl monoisostearate, glyceryl distearate, and glycerol malate monostearate), polyglycerin fatty acid esters (e.g., diglyceryl monostearate, and hexaglyceryl tristearate), propylene glycol/pentaerythritol fatty acid esters (e.g., propylene glycol monostearate, and pentaerythritol stearate), polyethylene glycol fatty acid esters (e.g., POE (4) monostearate, and POE (2) monooleate), polyoxyethylene alkyl ethers (e.g., POE (2) cetyl ether, POE (5) behenyl ether, and POE (3) octylphenyl ether), polyoxyethylene castor oils/hydrogenated castor oils (such as POE (3) castor oil, and POE (5) hydrogenated castor oil), modified silicones with a silicone chain of a linear, branched or crosslinked type (e.g., polyether modified silicone, polyether/alkyl comodified silicone, polyglycerin modified silicone, and polyglycerin/alkyl comodified silicone), sucrose fatty acid esters, and the like.

One or more of types of component (D) may be used and included in an amount of 0.1 to 20% by weight, preferably 0.1 to 10% by weight, further preferably 0.5 to 10% by weight, and more preferably 1.3 to 2.3% by weight based on a total weight of the composition. These ranges are preferable from the viewpoint of improving dispersibility of component (B) in component (C) and component (G) (discussed below) and adhesion between component (A) and component (B) in an applying and drying process.

In embodiments, component (E) in O/W emulsified cosmetic compositions according to the present invention is a water-soluble polymer having a hydrocarbon group with a carbon number of 8 to 30 and an anionic group in a molecule thereof.

The hydrocarbon group with a carbon number of 8 to 30 may be linear or branched. Exemplary hydrocarbon groups include an alkyl group, an alkenyl group, an arylalkyl group, an alkylaryl group, and the like. The hydrocarbon group preferably includes a group with a carbon number of 10 to 26, and more preferably an alkyl group with a carbon number of 12 to 22.

Examples of the anionic group include a carboxyl group, a sulfonic group, a phosphoric group, and the like.

Examples of water-soluble polymers of component (E) include the following (E-1) and (E-2).

(E-1) A water-soluble polysaccharide derivative in which some or all of the hydrogen atoms of hydroxyl groups of a polysaccharide or a derivative thereof are substituted with (a) a substituent having a hydrophobic portion selected from the group consisting of a linear or branched alkyl group, alkenyl group, arylalkyl group, and alkylaryl group with a carbon number of 8 to 30, or (b) a substituent having an anionic hydrophilic portion optionally substituted with a hydroxyl group, and a ratio of substitution degree between substituent (a) and substituent (b) is 1:1000 to 100:1.

Examples of such water-soluble polysaccharide derivatives include the modified polysaccharide derivative into which an anionic group and a hydrophobic group are simultaneously introduced by the method described in JP-A 11-12119, the modified cellulose ether described in Examples 1 to 3 of JP-A 3-12401, the nonionic long-chain alkylated cellulose ether described in U.S. Pat. No. 4,228,277; alkyl-modified hydroxyethyl celluloses with anionic groups such as the commercial products NATROSOL PLUS 330 and NATROSOL PLUS CS D-67 (both manufactured by Aqualon Company); and the like. Commercial products such as sodium stearoxy PG-hydroxyethylcellulose sulfonate (INCI: SODIUM STEAROXY PG-HYDROXYETHYL-CELLULOSE SULFONATE) (POIZ 310 (manufactured by Kao Corporation)) may be also used.

(E-2) A polymer of acrylic acid and/or methacrylic acid having an alkyl group in a side chain.

More specific examples thereof include alkyl acrylate/alkyl methacrylate/polyoxyethylene (20) stearyl ether copolymer (INCI: ACRYLATES/STEARETH-20 METHACRYLATE COPOLYMER), alkyl acrylate/alkyl methacrylate/polyoxyethylene (25) lauryl ether copolymer (INCI: ACRYLATES/LAURETH-25 METHACRYLATE COPOLYMER), alkyl acrylate/alkyl methacrylate/polyoxyethylene (25) behenyl ether copolymer (INCI: ACRYLATES/BEHENETH-25 METHACRYLATE COPOLYMER), acrylic acid/alkyl methacrylate copolymer (INCI: ACRYLATES/C10-30 ALKYL ACRYLATE CROSSPOLYMER), acrylic acid/vinyl neodecanoate copolymer (INCI: ACRYLATES/VINYL NEODECANOATE CROSSPOLYMER), (alkyl acrylate/octylacrylamide) copolymer (INCI: ACRYLATES/OCTYLACRYLAMIDE COPOLYMER), (acrylates/steareth-20 itaconate) copolymer (INCI: ACRYLATES/STEARETH-20 ITACONATE COPOLYMER), (acrylates/ceteth-20 itaconate) copolymer (INCI: ACRYLATES/CETETH-20 ITACONATE COPOLYMER), (acrylates/aminoacrylates/C10-30 acryl PEG-20 itaconate) copolymer (INCI: ACRYLATES/AMINOACRYLATES/C10-30 ALKYL PEG-20 ITACONATE COPOLYMER), and the like.

Further examples include commercial products, such as Aculyn 88, Aculyn 22, Aculyn 28 and Aculyn 38 (each manufactured by Rohm and Haas Japan Company), Carbopol Ultrez 21, Carbopol Ultrez 20, PEMULEN TR-1 and PEMULEN TR-2 (each manufactured by Noveon Company), and STRUCTURE 2001, STRUCTURE 3001, STRUCTURE PLUS and DERMACRYL 79 (each manufactured by Japan NSC).

Among these, sodium stearoxy PG-hydroxyethylcellulose sulfonate, acrylic acid/alkyl methacrylate copolymer, and alkyl acrylate/alkyl methacrylate/polyoxyethylene (20) stearyl ether copolymer are preferable.

One or more of types of component (E) may be used and included in an amount of 0.05 to 10% by weight, preferably 0.1 to 5% by weight, further preferably 0.1 to 0.8% by weight, and more preferably 0.2 to 0.8% by weight based on a total weight of the composition from the viewpoint of temporal stability and a smooth feeling upon use.

In embodiments, component (F) in O/W emulsified cosmetic compositions according to the present invention is water. Water may be employed as the balance of other components and included preferably in an amount of 20 to 60% by weight, particularly 30 to 50% by weight based on a total weight of the composition from the viewpoint of obtaining an excellent moisture retaining property and a feeling upon use with less stickiness.

In embodiments, component (G) in O/W emulsified cosmetic compositions according to the present invention is a silicone oil. Silicone oils are preferably used in combination with oils of component (C) from the viewpoint of suppressing stickiness during application.

Such silicone oils are liquid at a temperature of 25° C. and have a viscosity of more than 0 and 500,000 mPa·s or less, preferably 100,000 mPa·s or less at a temperature of 25° C., similar to component (C). Exemplary silicone oils include dimethyl polysiloxane, cyclic dimethyl polysiloxane, methylphenyl polysiloxane, amino-modified silicone, epoxy-modified silicone, carboxy-modified silicone, alcohol-modified silicone, alkyl-modified silicone, and the like.

Among these, dimethyl polysiloxane and cyclic dimethyl polysiloxane are preferable.

One or more types of component (G) may be used and included in an amount of 5 to 40% by weight, and preferably 10 to 30% by weight, based on a total weight of the composition, from the viewpoint of suppressing a sticky feeling upon use.

A total content of component (C) and component (G) may be 10 to 50% by weight, and preferably 20 to 40% by weight based on a total weight of the composition from the viewpoint of obtaining an excellent feeling upon use.

In addition, a weight ratio between component (C) and component (G) is preferably (C)/(G)=0.005 to 5, and more preferably 0.01 to 1, from the viewpoint of enhancing the effects described above.

In addition, cosmetic compositions according to the present invention may include an organic ultraviolet absorber having absorption in a UVA region to further improve an ultraviolet protective effect and a moisture retaining property.

Either of oil-soluble and water-soluble compounds may be used as organic ultraviolet absorbers, oil-soluble compounds being preferable for enhancing the effects described above.

Examples of oil-soluble compounds include hexyl diethylaminohydroxybenzoylbenzoate, tert-butylmethoxydibenzoylmethane, bisethylhexyloxyphenol methoxyphenyltriazine, and the like.

Examples of water-soluble ultraviolet absorbers include phenylene-1,4-bis(2-benzimidazyl)-3,3'-5,5'-tetrasulfonic acid, a salt thereof, and the like.

One or more types of such ultraviolet absorber may be used and included in an amount of 0.1 to 10% by weight, preferably 0.5 to 5% by weight based on a total weight of the composition from the viewpoint of obtaining stable blending and a sufficient ultraviolet protective effect.

O/W emulsified cosmetic compositions according to the present invention preferably include a combination of preferable ranges of each component.

In a preferred embodiment, an O/W emulsified cosmetic composition according to the present invention includes:

(A) 1 to 20% by weight of a plate-like powder having an average particle diameter of 0.1 to 10 μm that has been surface-treated with alkylalkoxysilane, preferably 1 to 20% by weight of a plate-like powder made of zinc oxide, titanium dioxide, and/or cerium oxide, having an average particle diameter of 0.1 to 10 that has been surface-treated with alkylalkoxysilane, and more preferably 1 to 20% by weight of a plate-like powder made of zinc oxide, titanium dioxide and cerium oxide, having an average particle diameter of 0.1 to 10 μm that has been surface-treated with octyltriethoxysilane or octyltrimethoxysilane, (B) 0.1 to 10% by weight of an oil that is solid at a temperature of 25° C., (C) 0.3 to 50% by weight of an oil selected from the group consisting of a hydrocarbon oil, an ester oil, and an ether oil, each having a viscosity of 500,000 mPa·s or less at a temperature of 25° C., (D) 0.1 to 20% by weight of a nonionic surfactant having an HLB value of 4 to 8, (E) 0.05 to 10% by weight of a water-soluble polymer having a hydrocarbon group with a carbon number of 8 to 30 and an anionic group in a molecule thereof, and (F) water, in which a weight ratio between component (A) and component (B) is (B)/(A)=–0.01 to 5.

In a further preferred embodiment, an O/W emulsified cosmetic composition according to the present invention includes:

(A) 1 to 20% by weight of a plate-like powder having an average particle diameter of 0.1 to 10 μm that has been surface-treated with alkylalkoxysilane, (B) 0.1 to 10% by weight of an oil that is solid at a temperature of 25° C. selected from the group consisting of a ceramide selected from the group consisting of natural ceramides of type I to type VI, N-(2-hydroxy-3-hexadecyloxypropyl)-N-2-hydroxyethylhexadecanamide and N-(2-hydroxy-3-hexadecyloxypropyl)-N-2-hydroxyethyldecanamide, and analogs thereof, and a sterol selected from the group consisting of cholesterol, stigmasterol, and ergosterol, (C) 0.3 to 50% by weight of an oil selected from the group consisting of a hydrocarbon oil, an ester oil and an ether oil, each having a viscosity of 500,000 mPa·s or less at a temperature of 25° C., (D) 0.1 to 20% by weight of a nonionic surfactant having an HLB value of 4 to 8, (E) 0.05 to 10% by weight of a water-soluble polymer having a hydrocarbon group with a carbon number of 8 to 30 and an anionic group in a molecule thereof, and (F) water, in which a weight ratio between component (A) and component (B) is (B)/(A)=–0.01 to 5.

In a further preferred embodiment, an O/W emulsified cosmetic composition according to the present invention includes:

(A) 1 to 20% by weight of a plate-like powder having an average particle diameter of 0.1 to 10 μm that has been surface-treated with alkylalkoxysilane, (B) 0.1 to 10% by weight of an oil that is solid at a temperature of 25° C., (C) 0.3 to 50% by weight of an oil selected from the group consisting of a hydrocarbon oil, an ester oil, and an ether oil, each having a viscosity of 500,000 mPa·s or less at a temperature of 25° C., (D) 0.1 to 20% by weight of a nonionic surfactant having an HLB value of 4 to 8, (E) 0.05 to 10% by weight of a water-soluble polymer having a hydrocarbon group with a carbon number of 8 to 30 and an anionic group in a molecule thereof, selected from the group consisting of sodium stearoxy PG-hydroxyethylcellulose sulfonate, acrylic acid/alkyl methacrylate copolymer, and alkyl acrylate/alkyl methacrylate/polyoxyethylene (20) stearyl ether copolymer, and (F) water, in which a weight ratio between component (A) and component (B) is (B)/(A) 0.01 to 5.

In a further preferred embodiment, an O/W emulsified cosmetic composition according to the present invention includes:

(A) 1 to 20% by weight of a plate-like powder having an average particle diameter of 0.1 to 10 μm that has been surface-treated with alkylalkoxysilane, (B) 0.1 to 10% by weight of an oil that is solid at a temperature of 25° C., (C) 0.3 to 50% by weight of an oil selected from the group consisting of a hydrocarbon oil, an ester oil, and an ether oil, each having a viscosity of 500,000 mPa·s or less at a temperature of 25° C., (D) 0.1 to 20% by weight of a nonionic surfactant having an HLB value of 4 to 8, (E) 0.05 to 10% by weight of a water-soluble polymer having a hydrocarbon group with a carbon number of 8 to 30 and an anionic group in a molecule thereof, (F) water, and (G) 5 to 40% by weight of a silicone oil, in which a weight ratio between component (A) and component (B) is (B)/(A)=0.01 to 5.

In a further preferred embodiment, an O/W emulsified cosmetic composition according to the present invention includes:

component (A) in an amount of 1 to 20% by weight, preferably 5 to 15% by weight, component (B) in an amount of 0.1 to 10% by weight, preferably 0.3 to 5% by weight, component (C) in an amount of 0.3 to 50% by weight, preferably 0.5 to 40% by weight, component (D) in an amount of 0.1 to 20% by weight, preferably 0.5 to 10% by weight, component (E) in an amount of 0.05 to 10% by weight, preferably 0.1 to 5% by weight, a balance, or 20 to 60% by weight, preferably 30 to 50% by weight, of component (F), component (G) in an amount of 5 to 40% by weight, preferably 10 to 30% by weight, a weight ratio between component (A) and component (B) is (B)/(A)=0.01 to 5, preferably 0.02 to 1, a weight ratio between component (B) and component (C) is (B)/(C)=0.0025 to 2, preferably 0.01 to 1, a total content of component (C) and component (G) is (C)+(G)=10 to 50% by weight, preferably 20 to 40% by weight, and a weight ratio between component (C) and component (G) is (C)/(G)=0.005 to 5, preferably 0.01 to 1.

In a further preferred embodiment, an O/W emulsified cosmetic composition according to the present invention includes:

(A) 5 to 15% by weight of a plate-like powder made of zinc oxide, titanium dioxide, and/or cerium oxide, having an average particle diameter of 0.1 to 10 μm that has been surface-treated with octyltriethoxysilane or octyltrimethoxysilane, (B) 0.1 to 5% by weight of a ceramide selected from the group consisting of natural ceramides of type I to type VI, N-(2-hydroxy-3-hexadecyloxypropyl)-N-2-hydroxyethylhexadecanamide and N-(2-hydroxy-3-hexadecyloxypropyl)-N-2-hydroxyethyldecanamide, and analogs thereof, (C) 0.5 to 40% by weight of an oil selected from the group consisting of a hydrocarbon oil, an ester oil and an ether oil, each having a viscosity of 500,000 mPa·s or less at a temperature of 25° C., (D) 0.1 to 10% by weight of a nonionic surfactant having an HLB value of 4 to 8, (E) 0.1 to 5% by weight of sodium stearoxy PG-hydroxyethylcellulose sulfonate, and (F) a balance of water, in which a weight ratio between component (A) and component (B) is (B)/(A)=0.01 to 5.

In a further preferred embodiment, an O/W emulsified cosmetic composition according to the present invention includes:

(A) 5 to 15% by weight of a plate-like powder having an average particle diameter of 0.1 to 10 μm, being made of zinc oxide, titanium dioxide, and/or cerium oxide that has been surface-treated with octyltriethoxysilane or octyltrimethoxysilane, (B) 0.1 to 5% by weight of a ceramide selected from the group consisting of natural ceramides of type I to type VI, N-(2-hydroxy-3-hexadecyloxypropyl)-N-2-hydroxyethylhexadecanamide and N-(2-hydroxy-3-hexadecyloxypropyl)-N-2-hydroxyethyldecanamide, and analogs thereof, (C) 0.5 to 40% by weight of an oil selected from the group consisting of a hydrocarbon oil, an ester oil, and an ether oil, each having a viscosity of 500,000 mPa·s or less at a temperature of 25° C., (D) 0.1 to 10% by weight of a nonionic surfactant having an HLB value of 4 to 8, (E) 0.1 to 5% by weight of sodium stearoxy PG-hydroxyethylcellulose sulfonate, (F) a balance of water, and (G) 10 to 30% by weight of dimethyl polysiloxane and a cyclic silicone oil, in which a weight ratio between component (A) and component (B) is (B)/(A)=0.01 to 5.

In a further preferred embodiment, an O/W emulsified cosmetic composition according to the present invention includes:

(A) 5 to 15% by weight of a plate-like powder having an average particle diameter of 0.1 to 10 μm, being made of zinc oxide, titanium dioxide, and/or cerium oxide that has been surface-treated with octyltriethoxysilane or octyltrimethoxysilane, (B) 0.1 to 5% by weight of a ceramide selected from the group consisting of natural ceramides of type I to type VI, N-(2-hydroxy-3-hexadecyloxypropyl)-N-2-hydroxyethylhexadecanamide and N-(2-hydroxy-3-hexadecyloxypropyl)-N-2-hydroxyethyldecanamide, and analogs thereof, (C) 0.5 to 40% by weight of an oil selected from the group consisting of a hydrocarbon oil, an ester oil, and an ether oil, each having a viscosity of 500,000 mPa·s or less at a temperature of 25° C., (D) 0.1 to 10% by weight of a nonionic surfactant having an HLB value of 4 to 8, (E) 0.1 to 5% by weight of sodium stearoxy PG-hydroxyethylcellulose sulfonate, (F) a balance of water, and (G) 10 to 30% by weight of dimethyl polysiloxane and a cyclic silicone oil, in which:

a weight ratio between component (A) and component (B) is (B)/(A)=0.01 to 5, a weight ratio between component (B) and component (C) is (B)/(C)=0.01 to 1, a total content of component (C) and component (G) is (C)+(G)=20 to 40% by weight, and a weight ratio between component (C) and component (G) is (C)/(G)=0.01 to 1.

Exemplary O/W emulsified cosmetic compositions according to the present invention may further include other components used in ordinary cosmetic compositions in addition to the above-mentioned components. Examples thereof include a lower alcohol, a humectant, a chelating agent, a whitening agent, vitamins, other various medicinal components, a powder except the above, an antioxidant, a perfume, a preservative, a pH adjustor, a sequestering agent, a germicide, a coloring material, and the like.

O/W emulsified cosmetic compositions according to the present invention may be produced employing ordinary methods.

In embodiments, methods for producing cosmetic compositions according to the present invention may include preparing an aqueous phase by combining and warming a component (E) and a component (F), preparing an oil phase by combining and warming a component (B), a component (C), and a component (D), mixing the aqueous phase and the oil phase and homogenizing to form a mixture, cooling the mixture to room temperature, and adding a powder phase comprising a component (A) to the mixture and mixing to obtain a cosmetic composition. In such methods, component (A) may be a plate-like powder that has been surface-treated with an alkylalkoxysilane and may be present in a cosmetic composition in an amount of 1 to 20% by weight, component (B) may be an oil that is solid at a temperature of 25° C. and may be present in a cosmetic composition in an amount of 0.1 to 10% by weight, component (C) may be an oil selected from the group consisting of a hydrocarbon oil, an ester oil, and an ether oil, each having a viscosity of 500,000 mPa·s or less at a temperature of 25° C., and may be present in a cosmetic composition in an amount of 0.3 to 50% by weight, component (D) may be a nonionic surfactant having an HLB value of 8 or less and may be present in a cosmetic composition in an amount of 0.1 to 20% by weight, component (E) may be a water-soluble polymer having a hydrocarbon group with a carbon number of 8 to 30 and an anionic group in a molecule thereof and may be present in a cosmetic composition in an amount of 0.05 to 10% by weight, and component (F) may be water. A weight ratio of component (B) to component (A) ((B)/(A)) in a cosmetic composition may be from 0.01 to 5. Such exemplary methods may further include preparing a powder phase by dispersing component (A) in a component (G). Component (G) may be a silicone oil.

In alternative exemplary embodiments, methods for producing cosmetic compositions according to the present invention may include preparing an aqueous phase by combining and warming a component (E) and a component (F), preparing an oil phase by combining and warming a component (B) and a component (C), mixing the aqueous phase and the oil phase and homogenizing to form a mixture, cooling the mixture to room temperature, preparing a powder phase by dispersing a component (A) in a component (D), and adding the powder phase to the mixture and mixing to obtain a cosmetic composition. In such methods, component (A) may be a plate-like powder that has been surface-treated with an alkylalkoxysilane and may be present in a cosmetic composition in an amount of 1 to 20% by weight, component (B) may be an oil that is solid at a temperature of 25° C. and may be present in a cosmetic composition in an amount of 0.1 to 10% by weight, component (C) may be an oil selected from the group consisting of a hydrocarbon oil, an ester oil, and an ether oil, each having a viscosity of 500,000 mPa·s or less at a temperature of 25° C., and may be present in a cosmetic composition in an amount of 0.3 to 50% by weight, component (D) may be a nonionic surfactant having an HLB value of 8 or less and may be present in the cosmetic composition in an amount of 0.1 to 20% by weight, component (E) may be a water-soluble polymer having a hydrocarbon group with a carbon number of 8 to 30 and an anionic group in a molecule thereof and may be present in a cosmetic composition in an amount of 0.05 to 10% by weight, and component (F) may be water. A weight ratio of component (B) to component (A) ((B)/(A)) in a cosmetic composition may be from 0.01 to 5. Such methods may further include preparing a powder phase by dispersing component (A) in component (D) and a component (G). Component (G) may be a silicone oil.

Of course, the exemplary methods described above may be modified, for example, by adding or omitting steps, adding or omitting components, or substituting components, component amounts, and techniques for components, component amounts, and techniques described herein.

EXAMPLES

In the following examples, and throughout this specification, all parts and percentages are by weight, and all temperatures are in degrees Celsius, unless expressly stated to be otherwise. Where the solids content of a dispersion or solution is reported, it expresses the weight of solids based on the total weight of the dispersion or solution, respectively. Where a molecular weight is specified, it is the molecular weight range ascribed to the product by the commercial supplier, which is identified. Generally this is believed to be weight average molecular weight.

Production Example 1

Production of Plate-Like Zinc Oxide $1.6 \times 10^{-1}$ mol of zinc sulfate, $3.8 \times 10^{-2}$ mol of sodium sulfate, and $1.6 \times 10^{-4}$ mol of ferrous sulfate as a salt of a trace element were dissolved in 315 mL of a $5 \times 10^{-2}$ mol sulfuric acid aqueous solution.

Next, while stirring this solution at 6000 r.p.m. with a homomixer, 230 mL of a 2N-sodium hydroxide aqueous solution was poured in over 15 seconds (pH=12.8) to produce a precipitate and thereafter continue stirring for 10 minutes. Thereafter, this solution was aged at a temperature of 100° C. for 90 minutes, filtered, washed in water, and dried at a temperature of 230° C. for approximately 10 hours to obtain plate-like zinc oxide. The powder thus obtained was observed with a scanning electron microscope and confirmed to be a flake-like particle. The average particle diameter of the obtained powder was 0.25 μm and the plate ratio was 13.

Production Example 2

Production of Octylsilylated Plate-Like Zinc Oxide

A slurry containing 93% by weight of the plate-like zinc oxide powder obtained in Production Example 1, 7% by weight of octyltriethoxysilane, and toluene was prepared, milled and pulverized using a bead mill (DYNO-MILL, manufactured by SHINMARU ENTERPRISES CORPORATION). Subsequently, toluene was distilled off by heating under reduced pressure, and thereafter the slurry was heat-treated by using a circulation flash dryer at a temperature of 150° C. for 4 hours to obtain octylsilylated plate-like zinc oxide powder.

The powder thus obtained was observed with a scanning electron microscope and confirmed to be a flake-like particle. The average particle diameter of the obtained powder was 0.20 μm and the plate ratio was 10.

Production Example 3

Production of Silicone-Treated Plate-Like Zinc Oxide

A slurry containing 98 parts by weight of the plate-like zinc oxide powder obtained in Production Example 1, 2 parts by weight of methylhydrogen polysiloxane (KF-99P, manufactured by Shin-Etsu Chemical Co., Ltd.), and isopropyl alcohol was prepared, stirred well and milled. Subsequently, the solvent was distilled off by heating under reduced pressure, and thereafter the slurry was heat-treated in air at a temperature of 150° C. for 4 hours to obtain silicone-treated plate-like zinc oxide.

Production Example 4

Production of Octylsilylated Talc

A slurry containing 98% by weight of a talc powder (FK-500S, manufactured by YAMAGUCHI MICA CO., LTD.), 2% by weight of octyltriethoxysilane, and toluene was prepared, milled and pulverized using a bead mill (DYNO-MILL, manufactured by SHINMARU ENTERPRISES CORPORATION). Subsequently, toluene was distilled off by heating under reduced pressure, and thereafter the slurry was heat-treated by using a circulation flash dryer at a temperature of 150° C. for 4 hours to obtain octylsilylated talc powder.

The powder thus obtained was observed with a scanning electron microscope and confirmed to be a flake-like particle. The average particle diameter of the obtained powder was 10 μm and the plate ratio was 45.

Examples 1 to 2 and Comparative Examples 1 to 8

O/W emulsified cosmetic compositions having the compositions shown in TABLE 1 were produced by the method described below to evaluate ultraviolet protective effect, moisture transpiration rate, and a lack degree of dryness. The results are shown together in TABLE 1.

As evidenced by these results, cosmetic compositions according to the present invention are high in ultraviolet protection and excellent in a moisture retaining property due to the use of a plate-like powder that has been surface-treated with alkylalkoxysilane and an oil that is solid at a temperature of 25° C. in combination with a specific liquid oil and emulsifying agent.

(Production Method)

A water-soluble component containing component (E), a water-soluble polymer, was completely dissolved in purified water warmed to a temperature of 80° C., and a polyol was further added thereto and homogenized into an aqueous phase. The obtained aqueous phase was moved to an agihomomixer, to which an oil phase (containing component (B), a solid oil, component (C), a liquid oil, and component (D), a nonionic surfactant) previously dissolved while stirred at a temperature of 80° C. was further added while stirring little by little. After completion of addition, the solution was stirred at high speed with an agihomomixer and cooled to room temperature. A powder phase was prepared by uniformly dispersing component (A), a powder, in a mixed solution of component (G), methyl polysiloxane, N-propionylpolyethyleneimine/methyl polysiloxane copolymer, and ethanol. The power phase was added and the resulting mixture was stirred at high speed with an agihomomixer and degassed to obtain an O/W emulsified cosmetic composition.

(Evaluation Method)

(1) Ultraviolet Protective Effect:

Each cosmetic composition was applied onto a quartz plate so as to have a thickness of 2 mg/cm$^2$ to measure total transmitted light spectrum by using an SPF analyzer (manufactured by Optometrics Corporation) and then obtain protection in a UVB range, protection in a UVA range and transparency of visible light from transmittance at a wavelength of 300 nm, 370 nm and 450 nm, respectively.

(2) Moisture Transpiration Rate (Occlusive Properties):

20 mL of water was poured into a 40-mL vial. 0.03 mL of each cosmetic composition was applied to a cellulose membrane filter with a diameter of 2.2 cm (A300A142C, manufactured by Toyo Roshi Kaisha, Ltd.). Each filter was placed in a lid with a hole (a circle with a diameter of 1.4 cm) and the lid was placed on the vial.

The vial was preserved for two days under conditions of a temperature of 30° C. and a humidity of 40% to measure the weight before and after preservation and then calculate moisture transpiration amount. The moisture transpiration amount in applying only water to the filter was regarded as 100 to obtain moisture transpiration rate by the following expression. When this value was smaller, it was shown that occlusive properties of moisture are higher and moisture retention is superior.

Moisture transpiration rate(%)=(moisture transpiration amount of sample/moisture transpiration amount of water)×100

(3) Lack Degree of Dryness:

Five special panelists applied 1 g of each cosmetic composition to their hands, and each of the panelists functionally evaluated the degree of dryness and determines by five degrees of 1 to 5 while offering one point to the case of great dryness and five points to the case of no dryness. This point was subjected to arithmetic mean, and the value obtained by rounding off the decimal point of the mean point was regarded as the evaluation result. A greater value indicated greater suppression of dryness.

TABLE 1

| | Components (% by weight) | Example 1 | Comparative Example 1 | Comparative Example 2 | Comparative Example 3 | Comparative Example 4 |
|---|---|---|---|---|---|---|
| A | Octylsilylated plate-like zinc oxide (Production Example 2) | 10.0 | | | 10.0 | 10.0 |
| B | N-(hexadecyloxyhydroxypropyl)-N-hydroxyethylhexadecanamide*[1] | 0.5 | 0.5 | 0.5 | | 0.5 |
| | 2-ethylhexyl paramethoxycinnamate*[2] | | | | | |
| | Hexyl diethylaminohydroxybenzoylbenzoate*[3] | | | | | |
| C | Squalane*[4] | 5.0 | 5.0 | 5.0 | 5.0 | |
| D | Sorbitan stearate*[5] | 0.3 | 0.3 | 0.3 | 0.3 | 0.3 |
| D | Polyoxyethylene/methyl polysiloxane copolymer*[6] | 1.0 | 1.0 | 1.0 | 1.0 | 1.0 |
| G | Methyl cyclopolysiloxane*[7] | 30.0 | 30.0 | 30.0 | 30.5 | 35.0 |
| | Silicone-coated plate-like zinc oxide (Production Example 3) | | 10.0 | | | |
| | Octylsilylated finezinc oxide*[8] | | | 10.0 | | |
| | N-propionylpolyethyleneimine/methyl polysiloxane copolymer*[9] | 0.4 | 0.4 | 0.4 | 0.4 | 0.4 |
| | Ethanol | 1.0 | 1.0 | 1.0 | 1.0 | 1.0 |
| E | Sodium stearoxy PG-hydroxyethylcellulose sulfonate*[10] | 0.4 | 0.4 | 0.4 | 0.4 | 0.4 |

TABLE 1-continued

|   | Components (% by weight) | | | | | |
|---|---|---|---|---|---|---|
|   | Glycerin | 4.3 | 4.3 | 4.3 | 4.3 | 4.3 |
|   | 1,3-butylene glycol | 10.0 | 10.0 | 10.0 | 10.0 | 10.0 |
| F | Purified water | Balance | Balance | Balance | Balance | Balance |
|   | Total | 100 | 100 | 100 | 100 | 100 |
|   | (B)/(A) | 0.05 | — | — | — | 0.05 |
|   | (B)/(C) | 0.1 | 0.1 | 0.1 | — | — |
|   | UVB protective effect (T % 300 nm) | 10.9 | 16.8 | 17.2 | 11.8 | 12.1 |
|   | UVA protective effect (T % 370 nm) | 10.2 | 15.4 | 19.8 | 11.1 | 11.3 |
|   | Transparency (T % 450 nm) | 75.1 | 71.4 | 83.7 | 75.9 | 75.3 |
|   | Moisture transpiration rate (%) | 80.1 | 91.8 | 93.4 | 90.5 | 99.5 |
|   | Lack degree of dryness | 5 | 3 | 3 | 2 | 3 |

|   | Components (% by weight) | Example 2 | Comparative Example 5 | Comparative Example 6 | Comparative Example 7 | Comparative Example 8 |
|---|---|---|---|---|---|---|
| A | Octylsilylated plate-like zinc oxide (Production Example 2) | 10.0 | | | 10.0 | 10.0 |
| B | N-(hexadecyloxyhydroxypropyl)-N-hydroxyethylhexadecanamide*¹ | 0.5 | 0.5 | 0.5 | | 0.5 |
|   | 2-ethylhexyl paramethoxycinnamate*² | 3.0 | 3.0 | 3.0 | 3.0 | 3.0 |
|   | Hexyl diethylaminohydroxybenzoylbenzoate*³ | 1.0 | 1.0 | 1.0 | 1.0 | 1.0 |
| C | Squalane*⁴ | 5.0 | 5.0 | 5.0 | 5.0 | |
| D | Sorbitan stearate*⁵ | 0.3 | 0.3 | 0.3 | 0.3 | 0.3 |
| D | Polyoxyethylene/methyl polysiloxane copolymer*⁶ | 1.0 | 1.0 | 1.0 | 1.0 | 1.0 |
| G | Methyl cyclopolysiloxane*⁷ | 26.0 | 26.0 | 26.0 | 26.5 | 31.0 |
|   | Silicone-coated plate-like zinc oxide (Production Example 3) | | 10.0 | | | |
|   | Octylsilylated finezinc oxide*⁸ | | | 10.0 | | |
|   | N-propionylpolyethyleneimine/methyl polysiloxane copolymer*⁹ | 0.4 | 0.4 | 0.4 | 0.4 | 0.4 |
|   | Ethanol | 1.0 | 1.0 | 1.0 | 1.0 | 1.0 |
| E | Sodium stearoxy PG-hydroxyethylcellulose sulfonate*¹⁰ | 0.4 | 0.4 | 0.4 | 0.4 | 0.4 |
|   | Glycerin | 4.3 | 4.3 | 4.3 | 4.3 | 4.3 |
|   | 1,3-butylene glycol | 10.0 | 10.0 | 10.0 | 10.0 | 10.0 |
| F | Purified water | Balance | Balance | Balance | Balance | Balance |
|   | Total | 100 | 100 | 100 | 100 | 100 |
|   | (B)/(A) | 0.05 | — | — | — | 0.05 |
|   | (B)/(C) | 0.1 | 0.1 | 0.1 | — | — |
|   | UVB protective effect (T % 300 nm) | 2.13 | 2.39 | 2.61 | 2.32 | 2.52 |
|   | UVA protective effect (T % 370 nm) | 8.95 | 12.7 | 16.0 | 11.6 | 11.4 |
|   | Transparency (T % 450 nm) | 77.3 | 74.5 | 86.5 | 79.2 | 79.0 |
|   | Moisture transpiration rate (%) | 73.8 | 92.7 | 91.5 | 94.3 | 98.1 |
|   | Lack degree of dryness | 5 | 3 | 3 | 2 | 3 |

*¹SOFCARE ceramide SLE (manufactured by Kao Corporation)
*²Uvinul MC80 (manufactured by BASF)
*³Uvinul A Plus (manufactured by BASF)
*⁴Nikkol squalane (manufactured by Nikko Chemicals Co., Ltd.)
*⁵RHEODOL SP-S10V (manufactured by Kao Corporation) HLB 4.7
*⁶Silicone KF-6015 (manufactured by Shin-Etsu Chemical Co., Ltd.) HLB 4
*⁷Silicone TSF405A (manufactured by Momentive Performance Materials Inc.)
*⁸Powder in which the surface of fine zinc oxide ZnO-350 (manufactured by Sumitomo Osaka Cement Co., Ltd.) is octylsilylated
*⁹POLYSILICONE-9 (INCI name, manufactured by Kao Corporation)
*¹⁰POIZ 310 (manufactured by Kao Corporation)

Examples 3 to 10

O/W emulsified cosmetic compositions having the compositions shown in TABLE 2 were produced in the same manner as in Examples 1 and 2 to evaluate moisture transpiration rate and a lack degree of dryness for the obtained compositions. The results are shown together in TABLE 2.

Each of the obtained compositions was excellent in transparency and high in ultraviolet protective effect.

TABLE 2

| | Components (% by weight) | Example 3 | Example 4 | Example 5 | Example 6 | Example 7 | Example 8 | Example 9 | Example 10 |
|---|---|---|---|---|---|---|---|---|---|
| A | Octylsilylated plate-like zinc oxide (Production Example 2) | 10 | 1 | 20 | 5 | 5 | 2 | 15 | |
| A | Octylsilylated talc*¹¹ | | | | | | | | 3 |

TABLE 2-continued

| | Components (% by weight) | Example 3 | Example 4 | Example 5 | Example 6 | Example 7 | Example 8 | Example 9 | Example 10 |
|---|---|---|---|---|---|---|---|---|---|
| B | N-(hexadecyloxyhydroxypropyl)-N-hydroxyethylhexadecanamide*1 | 0.1 | 0.1 | 0.3 | 0.1 | 5 | 10 | 0.5 | 0.4 |
| | Hexyl diethylaminohydroxybenzoylbenzoate*3 | | | | | | | | |
| | 2-ethylhexyl parametoxycinnamate*2 | 3 | | 3 | | | 3 | | 3 |
| C | Squalane*4 | 8 | 0.3 | 3 | 0.5 | | 10 | 8 | 13 |
| C | Isotridecyl isononanoate*12 | | | | | | | | 22 |
| C | Neopentylglycol dicaprate*13 | | | | | 10 | | | |
| C | Isododecane*14 | | | | | | | | 5 |
| D | Sorbitan stearate*5 | 0.3 | 0.5 | 0.3 | 0.1 | 1 | 1 | 0.3 | |
| D | Polyoxyethylene/methyl polysiloxane copolymer*6 | 1 | 1 | 1 | 0.4 | 9 | 1 | 1 | 0.1 |
| D | Polyoxyethylene cetyl ether*15 | | | | | | 0.1 | | |
| E | Sodium stearoxy PG-hydroxyethylcellulose sulfonate*10 | 0.4 | 0.1 | 0.5 | 0.4 | 0.8 | 0.6 | 5 | |
| E | (Alkyl acrylate/steareth methacrylate-20) copolymer*16 | | | | | | | | 0.9 |
| G | Methyl cyclopolysiloxane*7 | 26 | 30 | 25 | 19.5 | 10 | 27 | 25 | 5 |
| G | Methyl polysiloxane (2cs)*17 | | | | | | | | |
| G | Methyl polysiloxane (6cs)*18 | | | | | | 3 | | |
| | Silicone-coated plate-like zinc oxide (Production Example 3) | | 1 | | | | 3 | | |
| | Silicone-treated fine zinc oxide*8 | | 3 | | | | | | |
| | N-propionylpolyethyleneimine/methyl polysiloxane copolymer*9 | 0.4 | 0.4 | 0.4 | 0.4 | | 0.4 | 0.4 | |
| | Hydroxyethyl cellulose*19 | | 0.3 | | | | | | |
| | Xanthan gum*20 | | 0.5 | | | | | | |
| | Potassium hydroxide | | | | | | | | 0.19 |
| | PEG-40 hydrogenated castor oil*21 | | | | | | | 1 | |
| | Ethanol | 1 | 1 | 1 | 1 | | | 3.75 | |
| | Glycerin | 4.3 | 4.3 | 0.5 | 4.3 | 4.3 | 0.5 | 0.5 | 0.5 |
| | 1,3-butylene glycol | 10 | 10 | 10 | 10 | 10 | 5 | 10 | 5 |
| F | Purified water | Balance | Balance | Balance | Balance | Balance | Balance | Balance | Balance |
| | Total | 100 | 100 | 100 | 100 | 100 | 100 | 100 | 100 |
| | (B)/(A) | 0.01 | 0.1 | 0.015 | 0.02 | 1.0 | 5.0 | 0.33 | 0.13 |
| | (B)/(C) | 0.013 | 0.33 | 0.1 | 0.2 | 0.5 | 1.0 | 0.63 | 0.01 |
| | Moisture transpiration rate (%) | 84.6 | 84.2 | 82.6 | 83.2 | 78.3 | 64.2 | 56.8 | 82.3 |
| | Lack degree of dryness | 5 | 5 | 5 | 5 | 5 | 5 | 5 | 5 |

TABLE 3

11: Powder in which the surface of Talc F (manufactured by NIPPON TALC Co.,Ltd.) is octylsilylated 12: Salacos 913 (manufactured by The Nisshin OilliO Group, Ltd.)

13: ESTEMOL N-01 (manufactured by The Nisshin OilliO Group, Ltd.)

14: MARUKASOL R (manufactured by Maruzen Petrochemical Co., Ltd.)

15: Nikkol BC-2 (manufactured by Nikko Chemicals Co., Ltd.; HLB 8)

16: Aculyn 22 (manufactured by Rohm and Haas Japan Company)

17: Silicone KF-96L-2CS (manufactured by Shin-Etsu Chemical Co., Ltd.)

18: Silicone KF-96A-6CS (manufactured by Shin-Etsu Chemical Co., Ltd.)

19: HEC Daicel SE400 (manufactured by Daicel Corporation)

20: ECHO GUM T (manufactured by Dainippon Sumitomo Pharma Co., Ltd.)

21: EMANON CH-40 (manufactured by Kao Corporation; HLB 12.5)

Examples 11 to 15

O/W emulsified cosmetic compositions having the compositions described below were produced by the same method as in Examples 1 to 2. Each of the obtained compositions was excellent in ultraviolet protective effect and high in moisture retention.

TABLE 4

| | Example 11 |
|---|---|
| (Components) | (% by weight) |
| N-(hexadecyloxyhydroxypropyl)-N-hydroxyethylhexadecanamide (SOFCARE ceramide SLE, manufactured by Kao Corporation) | 0.5 |
| 2-ethylhexyl parametoxycinnamate (Uvinul MC80, manufactured by BASF) | 3.0 |
| tert-Butylmethoxydibenzoylmethane (Parsol 1789, manufactured by DSM Nutrition Japan K.K.) | 0.5 |
| Bisethylhexyloxyphenol methoxyphenyltriazine (TINOSORB S, manufactured by Ciba Specialty Chemicals) | 0.5 |
| Isotridecyl isononanoate (Salacos 913, manufactured by The Nisshin OilliO Group, Ltd.) | 1.5 |
| Sorbitan stearate (RHEODOL SP-S10V, manufactured by Kao Corporation; HLB 4.7) | 0.3 |
| Polyoxyethylene/methyl polysiloxane copolymer (Silicone KF-6015 (manufactured by Shin-Etsu Chemical Co., Ltd.) HLB 4) | 1.0 |
| Methyl cyclopolysiloxane (Silicone TSF405A, manufactured by Momentive Performance Materials Inc.) | 23.5 |
| Methyl polysiloxane (6cs) (Silicone KF-96L-6CS, manufactured by Shin-Etsu Chemical Co., Ltd.) | 6.0 |
| Octylsilylated plate-like zinc oxide (Production Example 2) | 9.0 |
| N-propionylpolyethyleneimine/methyl polysiloxane copolymer (POLYSILICONE-9 (INCI name, manufactured by Kao Corporation) | 0.4 |
| Ethanol | 3.5 |

TABLE 4-continued

Example 11

| (Components) | (% by weight) |
|---|---|
| Sodium stearoxy PG-hydroxyethylcellulose sulfonate (POIZ 310, manufactured by Kao Corporation) | 0.4 |
| Glycerin | 4.3 |
| 1,3-butylene glycol | 5.0 |
| Purified water | Balance |
| Total | 100 |

((B)/(A) = 0.06)

TABLE 5

Example 12

| (Components) | (% by weight) |
|---|---|
| N-(hexadecyloxyhydroxypropyl)-N-hydroxyethylhexadecanamide (SOFCARE ceramide SLE, manufactured by Kao Corporation) | 0.5 |
| 2-ethylhexyl paramethoxycinnamate (Uvinul MC80, manufactured by BASF) | 3.0 |
| Hexyl diethylaminohydroxybenzoylbenzoate (Uvinul A Plus, manufactured by BASF) | 0.5 |
| Squalane (Nikkol squalane, manufactured by Nikko Chemicals Co., Ltd.) | 1.0 |
| Isotridecyl isononanoate (Salacos 913, manufactured by The Nisshin OilliO Group, Ltd.) | 1.0 |
| Di(cholesteryl/octyldodecyl) lauroylglutamate (Eldew CL-202, manufactured by Ajinomoto Co., Inc.) | 1.5 |
| Cholesteryl isostearate (EXEPARL IS-CE-A, manufactured by Kao Corporation) | 0.2 |
| Sorbitan stearate (RHEODOL SP-S10V, manufactured by Kao Corporation; HLB 4.7) | 0.3 |
| Polyoxyethylene/methyl polysiloxane copolymer (Silicone KF-6015, manufactured by Shin-Etsu Chemical Co., Ltd.; HLB 4) | 1.0 |
| Methyl cyclopolysiloxane (Silicone TSF405A, manufactured by Momentive Performance Materials Inc.) | 18.3 |
| Methyl polysiloxane (6cs) (Silicone KF-96L-6CS, manufactured by Shin-Etsu Chemical Co., Ltd.) | 6.0 |
| Octylsilylated plate-like zinc oxide (Production Example 2) | 9.0 |
| Octylsilylated talc (Production Example 4) | 3.0 |
| N-propionylpolyethyleneimine/methyl polysiloxane copolymer (POLYSILICONE-9 (INCI name, manufactured by Kao Corporation) | 0.4 |
| Ethanol | 3.5 |
| Sodium stearoxy PG-hydroxyethylcellulose sulfonate (POIZ 310, manufactured by Kao Corporation) | 0.4 |
| Glycerin | 4.3 |
| 1,3-butylene glycol | 5.0 |
| Purified water | Balance |
| Total | 100 |

((B)/(A) = 0.04)

TABLE 6

Example 13

| (Components) | (% by weight) |
|---|---|
| N-(hexadecyloxyhydroxypropyl)-N-hydroxyethylhexadecanamide (SOFCARE ceramide SLE, manufactured by Kao Corporation) | 1.0 |
| 2-ethylhexyl paramethoxycinnamate (Uvinul MC80, manufactured by BASF) | 3.0 |
| Hexyl diethyl aminohydroxybenzoylbenzoate (Uvinul A Plus, manufactured by BASF) | 1.0 |
| Squalane (Nikkol squalane, manufactured by Nikko Chemicals Co., Ltd.) | 2.0 |
| Isotridecyl isononanoate (Salacos 913, manufactured by The Nisshin OilliO Group, Ltd.) | 1.0 |

TABLE 6-continued

Example 13

| (Components) | (% by weight) |
|---|---|
| Di(cholesteryl/octyldodecyl) lauroylglutamate (Eldew CL-202, manufactured by Ajinomoto Co., Inc.) | 1.5 |
| Hydrogenated polyisobutene (IP solvent 2028, manufactured by Idemitsu Kosan Co., Ltd.) | 10.0 |
| Cholesteryl isostearate (EXEPARL IS-CE-A, manufactured by Kao Corporation) | 1.0 |
| Sorbitan stearate (RHEODOL SP-S10V, manufactured by Kao Corporation; HLB 4.7) | 0.3 |
| Polyoxyethylene/methyl polysiloxane copolymer (Silicone KF-6015 (manufactured by Shin-Etsu Chemical Co., Ltd.) HLB 4) | 2.0 |
| Methyl cyclopolysiloxane (Silicone TSF405A, manufactured by Momentive Performance Materials Inc.) | 10.0 |
| Methyl polysiloxane (6cs) (Silicone KF-96L-6CS, manufactured by Shin-Etsu Chemical Co., Ltd.) | 3.0 |
| Octylsilylated plate-like zinc oxide (Production Example 2) | 5.0 |
| Silicone-coated fine zinc oxide (Powder in which the surface of fine zinc oxide MZ500 (manufactured by TAYCA CORPORATION) is silicone-coated) | 5.0 |
| N-propionylpolyethyleneimine/methyl polysiloxane copolymer (POLYSILICONE-9 (INCI name, manufactured by Kao Corporation) | 0.4 |
| Ethanol | 1.0 |
| Sodium stearoxy PG-hydroxyethylcellulose sulfonate (POIZ 310, manufactured by Kao Corporation) | 0.4 |
| Glycerin | 8.6 |
| 1,3-butylene glycol | 10.0 |
| Purified water | Balance |
| Total | 100 |

((B) /(A) = 0.2)

TABLE 7

Example 14

| (Components) | (% by weight) |
|---|---|
| N-(hexadecyloxyhydroxypropyl)-N-hydroxyethylhexadecanamide (SOFCARE ceramide SLE, manufactured by Kao Corporation) | 2.0 |
| Paraffin wax | 0.5 |
| Cetyl alcohol | 0.6 |
| Stearyl alcohol | 0.4 |
| 2-ethylhexyl paramethoxycinnamate (Uvinul MC80, manufactured by BASF) | 2.0 |
| Hexyl diethylaminohydroxybenzoylbenzoate (Uvinul A Plus, manufactured by BASF) | 0.5 |
| Squalane (Nikkol squalane, manufactured by Nikko Chemicals Co., Ltd.) | 3.0 |
| Isotridecyl isononanoate (Salacos 913, manufactured by The Nisshin OilliO Group, Ltd.) | 5.0 |
| Sorbitan stearate (RHEODOL SP-S10V, manufactured by Kao Corporation; HLB 4.7) | 0.2 |
| Methyl polysiloxane (6cs) (Silicone KF-96L-6CS, manufactured by Shin-Etsu Chemical Co., Ltd.) | 10.0 |
| Octylsilylated talc (The one that Talc F (manufactured by NIPPON TALC Co., Ltd.) is octylsilylated) | 5.0 |
| Carbomer (Carbopol 981, manufactured by Lubrizol Corporation) | 0.1 |
| (Acrylic acid/alkyl acrylate (C10-30)) copolymer (PEMULEN TR-2, manufactured by Lubrizol Corporation) | 0.2 |
| Potassium hydroxide | 0.15 |
| Glycerin | 13.0 |
| Methyl parahydroxybenzoate | 0.3 |
| Purified water | Balance |
| Total | 100 |

((B)/(A) = 0.7)

TABLE 8

Example 15

| (Components) | (% by weight) |
|---|---|
| N-(hexadecyloxyhydroxypropyl)-N-hydroxyethylhexadecanamide (SOFCARE ceramide SLE, manufactured by Kao Corporation) | 0.5 |
| 2-ethylhexyl paramethoxycinnamate (Uvinul MC80, manufactured by BASF) | 3.0 |
| Hexyl diethylaminohydroxybenzoylbenzoate (Uvinul A Plus, manufactured by BASF) | 0.5 |
| Squalane (Nikkol squalane, manufactured by Nikko Chemicals Co., Ltd.) | 10.0 |
| Isotridecyl isononanoate (Salacos 913, manufactured by The Nisshin OilliO Group, Ltd.) | 10.0 |
| Di(cholesteryl/octyldodecyl) lauroylglutamate (Eldew CL-202, manufactured by Ajinomoto Co., Inc.) | 1.5 |
| Cholesteryl isostearate (EXEPARL IS-CE-A, manufactured by Kao Corporation) | 0.2 |
| Sorbitan stearate (RHEODOL SP-S10V, manufactured by Kao Corporation; HLB 4.7) | 0.3 |
| Polyoxyethylene/methyl polysiloxane copolymer (Silicone KF-6015 (manufactured by Shin-Etsu Chemical Co., Ltd.) HLB 4) | 1.0 |
| Octylsilylated plate-like zinc oxide (Production Example 2) | 9.0 |
| N-propionylpolyethyleneimine/methyl polysiloxane copolymer (POLYSILICONE-9 (INCI name, manufactured by Kao Corporation) | 0.4 |
| Ethanol | 3.5 |
| Sodium stearoxy PG-hydroxyethylcellulose sulfonate (POIZ 310, manufactured by Kao Corporation) | 0.4 |
| Glycerin | 4.3 |
| 1,3-butylene glycol | 5.0 |
| Purified water | Balance |
| Total | 100 |

((B)/(A) = 0.06)

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A cosmetic composition, comprising:
(A) from 5 to 15% by weight of a plate-like powder, wherein the plate-like powder is zinc oxide that has been surface-treated with octyltriethoxysilane;
(B) from 0.1 to 5% by weight of a ceramide analog;
(C) from 0.3 to 40% by weight of an oil selected from the group consisting of squalane, isododecane, isotridecyl isononanoate, and neopentylglycol dicaprate;
(D) from 0.1 to 10% by weight of a nonionic surfactant having an HLB value of 4 to 8 selected from the group consisting of a sorbitan fatty acid ester, polyoxyethylene alkyl ether, and polyether modified silicone;
(E) from 0.1 to 5% by weight of a water-soluble polymer selected from the group consisting of a sodium stearoxy PG-hydroxyethylcellulose sulfonate, acrylic acid/alkyl methacrylate copolymer, and alkyl acrylate/alkyl methacrylate/polyoxyethylene (20) stearyl ether copolymer; and
(F) water;
wherein a weight ratio of the ceramide analog (B) to the plate-like powder (A), (B)/(A), is from 0.01 to 1; and the cosmetic composition is in the form of an oil-in-water (O/W) emulsion.

2. The composition according to claim 1, wherein the plate-like powder (A) has an average particle diameter of 0.1 to 10 µm.

3. The composition according to claim 1, wherein the ceramide analog (B) comprises at least one ceramide selected from the group consisting of N-(2-hydroxy-3-hexadecyloxypropyl)-N-2-hydroxyethylhexadecanamide, and N-(2-hydroxy-3-hexadecyloxypropyl)-N-2-hydroxyethyldecanamide.

4. The composition according to claim 1, wherein the nonionic surfactant (D) is a sorbitan fatty acid ester.

5. The composition according to claim 1, comprising from 0.3 to 1.5% by weight of the ceramide analog (B).

6. The composition according to claim 1, comprising from 0.3 to 10% by weight of the oil (C).

7. The cosmetic composition according to claim 1, comprising from 0.5 to 10% by weight of the nonionic surfactant (D).

8. The composition according to claim 1, comprising from 0.1 to 0.8% by weight of the water-soluble polymer (E).

9. The composition according to claim 1, further comprising (G) at least one silicone oil selected from the group consisting of a cyclic dimethyl polysiloxane and dimethyl polysiloxane, each having a viscosity of 100,000 mPa·s or less at a temperature of 25° C.

10. The composition according to claim 9, comprising from 5.0 to 30.0% by weight of the silicone oil (G).

11. The composition according to claim 10, wherein a weight ratio of the oil (C) to the at least one silicone oil (G), (C)/(G), is from 0.01 to 5.

12. A cosmetic composition, comprising:
(A) from 5 to 15% by weight of a plate-like powder, wherein the plate-like powder is zinc oxide that has been surface-treated with octyltriethoxysilane;
(B) from 0.1 to 5% by weight of N-(2-hydroxy-3-hexadecyloxypropyl)-N-2-hydroxyethylhexadecanamide;
(C) from 0.3 to 40% by weight of an oil selected from the group consisting of squalane, isododecane, isotridecyl isononanoate, and neopentylglycol dicaprate;
(D) from 0.1 to 10% by weight of a nonionic surfactant selected from the group consisting of sorbitan stearate, polyoxyethylene/methyl polysiloxane copolymer, and polyoxyethylene cetyl ether;
(E) from 0.1 to 5% by weight of a water-soluble polymer selected from the group consisting of sodium stearoxy PG-hydroxyethylcellulose sulfonate, acrylic acid/alkyl methacrylate copolymer, and alkyl acrylate/alkyl methacrylate/polyoxyethelene (20) stearyl ether copolymer;
(F) water; and
wherein a weight ratio of the component (B) to the plate-like powder (A), (B)/(A), is from 0.01 to 1; and the cosmetic composition is in the form of an oil-in-water (O/W) emulsion.

13. The composition according to claim 12, further comprising (G) at least one silicone oil selected from the group consisting of methyl cyclopolysiloxane and methyl polysiloxane, wherein the methyl polysiloxane has a viscosity of 2 cs to 6 cs.

14. The composition according to claim 13, comprising from 5.0 to 30.0% by weight of the at least one silicone oil (G).

15. A cosmetic composition, comprising:
(A) from 9 to 12% by weight of a plate-like zinc oxide that has been surface-treated with octyltriethoxysilane;
(B) from 0.5 to 1.5% by weight of N-(2-hydroxy-3-hexadecyloxypropyl)-N-2-hydroxyethylhexadecanamide;
(C) from 5 to 10% by weight of an oil selected from the group consisting of squalane, isododecane, isotridecyl isononanoate, and neopentylglycol dicaprate;
(D) from 1.3 to 2.3% by weight of a nonionic surfactant selected from the group consisting of sorbitan stearate and polyoxyethylene/methyl polysiloxane copolymer;
(E) from 0.2 to 0.8% by weight of sodium stearoxy PG-hydroxyethylcellulose sulfonate;
(F) water; and
wherein a weight ratio of the component (B) to the plate-like zinc oxide (A), (B)/(A), is from 0.05 to 0.15; and the cosmetic composition is in the form of an oil-in-water (O/W) emulsion.

16. The cosmetic composition according to claim 15, wherein the oil (C) is squalane.

17. The composition according to claim 1, wherein the ceramide analog (B) is N-(hexadecyloxyhydroxypropyl)-N-hydroxyethylhexadecanamide.

* * * * *